Figure 1A:
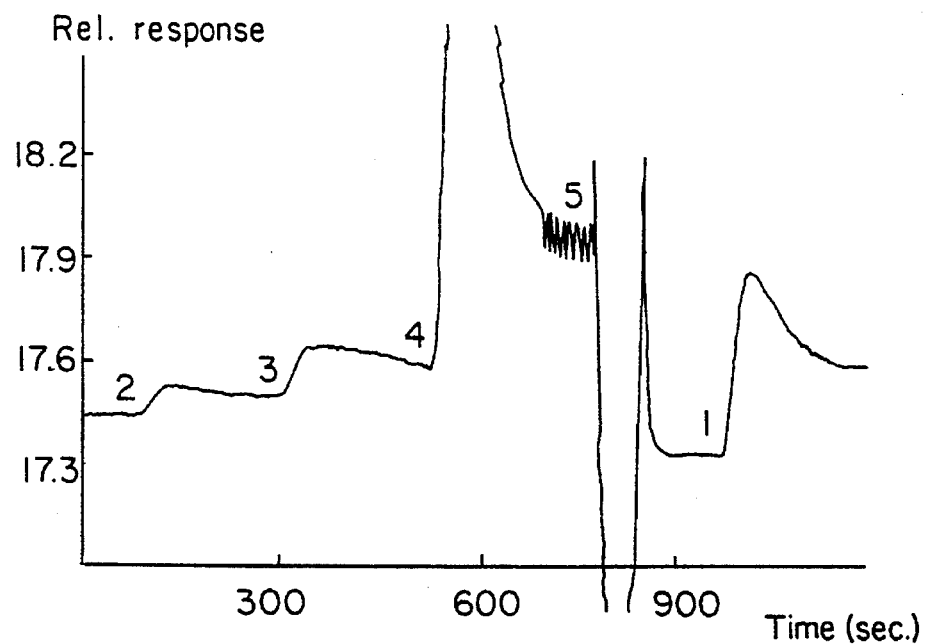

United States Patent [19]

Malmqvist et al.

[11] Patent Number: 5,554,541
[45] Date of Patent: Sep. 10, 1996

[54] CHARACTERIZING MACROMOLECULES INTERACTING WITH AT LEAST THREE LIGANDS ON A SENSOR

[75] Inventors: Magnus Malmqvist; Robert Karlsson; Anita Larsson, all of Upsala; Jörgen Sjödal, Knivsta, all of Sweden

[73] Assignee: Pharmacia Biosensor AB, Uppsala, Sweden

[21] Appl. No.: 366,443

[22] Filed: Dec. 30, 1994

Related U.S. Application Data

[63] Continuation of Ser. No. 681,530, May 10, 1991, abandoned.

[30] Foreign Application Priority Data

Nov. 10, 1988 [SE] Sweden ................................ 8804074
Jun. 5, 1989 [SE] Sweden ................................ 8902043

[51] Int. Cl.⁶ .................................................. G01N 33/543
[52] U.S. Cl. ................... 436/518; 422/82.05; 422/82.08; 422/82.11; 436/165; 436/527; 436/536; 436/805
[58] Field of Search ............................. 422/82.05, 82.08, 422/82.11; 436/165, 518, 527, 536, 805

[56] References Cited

U.S. PATENT DOCUMENTS

| | | | |
|---|---|---|---|
| 4,659,678 | 4/1987 | Forrest et al. | 436/512 |
| 5,104,790 | 4/1992 | Flesher et al. | 435/5 |

FOREIGN PATENT DOCUMENTS

| | | |
|---|---|---|
| 0142301 | 5/1985 | European Pat. Off. . |
| 0167248 | 1/1986 | European Pat. Off. . |
| 0184600 | 6/1986 | European Pat. Off. . |
| 0276142 | 7/1988 | European Pat. Off. . |
| 0276968 | 8/1988 | European Pat. Off. . |
| 0311768 | 4/1989 | European Pat. Off. . |
| 0026215 | 8/1985 | Sweden . |
| WO83/01112 | 3/1983 | WIPO . |
| WO87/02779 | 5/1987 | WIPO . |

OTHER PUBLICATIONS

Chemical Abstracts, vol. 109, No. 19, Abstract No. 166540v (1988).
Katchalski–Katzir et al, Bull. Chem. Soc. Jpn., vol. 61, pp. 133–139 (1988).
Fägerstam et al, "Biospecific interaction analysis using surface plasmon resonance detection . . . ", *Journal of Chromatography*, 597 (1992), pp. 397–410.
Wagener et al, "Monoclonal Antibodies For Carcinoembryonic Antigen & Related Antigens as a Model system . . . ", *Journal of Immunology*, 130(5), May 1983, pp. 2308–2315.
Oi and Herzenberg, "Localization of Marine Ig–1b and Ig–1a (IgG$_{2a}$) Allotypic Determinants Detected with Monoclonal Antibodies", *Molecular Immunology*, vol. 16, 1979, pp. 1005–1017.

*Primary Examiner*—James C. Housel
*Assistant Examiner*—Christopher L. Chin
*Attorney, Agent, or Firm*—Birch, Stewart, Kolasch & Birch, LLP

[57] ABSTRACT

A method of characterizing a macromolecule by studying its interactions with ligands comprises the determination of the mutual influence of ligand interactions by, after the macromolecule has interacted with at least one ligand, contacting the macromolecule with at least one additional ligand, either the macromolecule or the additional ligand or ligands having been bound to a sensor surface, determining interaction by detecting a consequential change in the physico-chemical properties of the sensor surface, and on the basis of the determined mutual dependence between the ligand interactions discriminating between epitopes of the macromolecule and mapping their relative positions.

14 Claims, 3 Drawing Sheets

CHARACTERIZING MACROMOLECULES INTERACTING WITH AT LEAST THREE LIGANDS ON A SENSOR

This application is a continuation of application Ser. No. 07/681,530 filed on May 10, 1991, now abandoned.

The present invention relates to the characterization of macromolecules, particularly proteins, and more particularly to a method of gaining structural information about macromolecules by studying their reactions with various ligands.

The characterization of proteins is today done mainly by two groups of techniques, viz., on one hand, composition informative techniques (aminoacid analysis, sequence analysis, spectrophotometry, massspectrometry), which all give the contents of chemical entities but no information about where these are located in the space, and, on the other hand, spacial structural methods (X-ray crystallography, NMR, cryoelectron microscopy, scanning electron tunneling microscopy), which depending on the particular method will provide various degrees of structural information. By X-ray crystallography the total spacial structure is certainly obtained, but the method requires transformation of the proteins into a crystalline form, which generally is difficult, and the method is further very time-consuming and laborious. Presently there are only about 400 proteins whose structures have been determined by X-ray crystallography with atomic resolution. Structural information with high resolution is obtained also by NMR, requiring the protein to be in solution. The resolution has hitherto been limited by the magnetic field of the apparatus, and the magnetic field cannot be infinitely strong, and by the size and the solubility of the proteins. Both NMR and X-ray crystallography additionally require pure proteins of a high quality and relatively large amounts thereof. Cryo-electron microscopy may provide surface structural information on protein in solid form by visual analysis, and scanning electron tunneling microscopy may possibly provide some information on protein in solid form. In summary these techniques for obtaining structural information about proteins are thus either complicated and time-consuming or will only provide limited information.

Structural information about proteins has also been obtained by immunological methods of analysis by means of antibodies specifically directed against a domain or region of the protein in question. For example, Furie B. et al. describe in Methods in Enzymology 84 (1982) 60–63 a study of conformational changes of prothrombin and Factor X by means of antibodies directed against specific determinants on the protein surface. Epitope mapping (i.e. determination of epitopes on the surface of a macromolecule) of human $\alpha_2$-macroglobulin by means of monoclonal antibodies and blotting technique is described by Van Leuven et al. in J. Immunol. 90 (1986) 125–130, while Mazza M. M and Retegui L. A. in Molec. Immun. 26 (1989) 231–240 describe epitope mapping of human growth hormon (hGH) by means of monoclonal antibodies and solid-phase RIA technique.

Recently optical methods for determining changes in the surface layer of a solid surface have begun to come into use in chemical and biochemical applications, e.g., for measuring the adsorption of tensides and proteins to various surfaces. Among these optical methods are ellipsometry and surface plasmon resonance technology (SPR). Ellipsometry is an old optical method rendering it possible to measure the refractive index of reflecting materials by measuring the change in mutual amplitude and phase relationships that the components of elliptic polarized light undergo when reflected against the surface. Upon adsorption of various substances to the surface, the amount adsorbed to the surface may be calculated as well as the thickness of the adsorbed layer. The surface plasmon resonance technique may, in somewhat simplified terms, be said to be a technique according to which changes in the refractive index of a layer close to a thin free-electron metal film are detected by way of the change of the intensity of a reflected p-polarized light beam that is caused by these refractive index changes (see, e.g. Raether H., I Physics of Thin Films, Ed. Hass G., Francombe M., and Hoffman R., Academic Press, New York, pages 145–261 (1977)). Hereinafter some publications will be described in which these techniques have been utilized in the chemical or biochemical field.

Cullen et al. describe in Biosensors 3 (1987/88) 211–225 the use of SPR techniques to detect immuno-complex formation in two model biochemical systems, in which human immunoglobulin G or the immunoglobulin fraction of sheep antiserum was physically adsorbed to a gold-coated diffraction grating. Affinity purified goat anti-human-IgG or human serum albumin, respectively, was subsequently specifically bound by immunocomplex formation, and the binding reactions could be followed with respect to time.

Daniels P. B. et al. describe in Sensors and Actuators, 15 (1988) 11–18, experiments where a concentration dependent change in surface plasmon resonance is obtained for the two systems avidin-immobilized biotin and alpha-feto protein immobilized antibody-antigen, which indicates the possibility of using SPR for a direct immunochemical analysis in solution.

Elwing H. et al. describe in J. Colloid Interface Sci., 125 (1988) 139–145, ellipsometric determination of conformational changes of the complement factor C3 adsorbed to hydrophilic and hydrophobic surfaces by means of antibodies directed against epitopes hidden in the native molecule.

Jönsson U. et al. describe in J. Colloid Interface Sci. 90 (1982) 148–163, the use of ellipsometry to study the adsorption of human fibronectin (HFN) to solid surfaces. Conformational changes of the protein upon adsorption were revealed by studying the interactions of the adsorbed protein with anti-HFN and concanavalin, respectively.

In Horrisberger M., Biochim. Biophys. Acta 632 (1980) 298–309, is described the use of ellipsometry for the investigation of the interaction of lectins with films of polysaccharides, glycopeptides and glycoproteins applied to a glass surface.

Mandenius, C. F. et al. describe in Anal. Biochem. 137 (1984) 106–114 the use of ellipsometry to study the interaction between proteins and cells with affinity ligands covalently coupled to silicon surfaces. The specific systems studied were concanavalin A-Saccharomyces cerevisiae-cells, immunoglobulin G-Staphylococcus aureus-cells and NAD-analogue-lactate dehydrogenase.

EP-B-26 215 discloses the use of a piezoelectric quartz crystal oscillator having an adsorbed layer of antigen thereon for determining the amount of an antigen specific antibody in a fluid sample.

Several of the above mentioned publications may quite principally be said to be examples of biosensor technology. A biosensor may be defined as a sensor capable of measuring the presence of biological molecules or particles in a sample and consists of a receptor for molecular recognition and a transducer. A group or type of biosensors is based upon detecting the changes occuring in the properties of a surface layer by the interaction of the receptor with the surrounding medium, such as by means of the above mentioned SPR and ellipsometry methods. Until now, however, biosensors in the proper sense have exclusively been used to detect or determine the concentration of a substance in a sample.

The present invention relates to the use of biosensor technology for a completely different purpose, viz. the characterization of macromolecules, such as proteins, with regard to exposed structural elements by studying the interactions of the macromolecules with various ligands and their mutual influence upon each other.

Before the invention is described in more detail part of the terminology used in connection with the definition of the invention will be explained.

The term macromolecule does not mean any real size limitation for the molecules it is intended to comprise, but generally refers to all large-sized molecules for which it is of interest to establish structural domains of the molecule. Examples are proteins (also including glycoproteins, lipoproteins, etc.), polypeptides, carbohydrates, lectins, polymers, DNA, RNA, etc., and the macromolecules may be natural as well as prepared synthetically.

Epitope refers to a defined surface-exposed structural element on a macromolecule. Certain epitopes—antigenic determinants—are characterized by their ability to bind to antibody molecules. Other epitopes may bind to other types of molecules. For example, glycosylated parts of a protein bind to certain lectins, certain exposed amino-acid residues chelate with metal ions, other epitopes constitute the biofunctional structure of the molecule and bind, e.g., to receptors or constitute a receptor binding site. The examples may easily be multiplied.

Ligand is a chemical compound which can interact with an epitope of a macromolecule. The ligand may itself exhibit one or more epitopes, through which the interactions take place. The ligand may, but need not, be a macromolecule. As examples of ligands may be mentioned natural ligands such as substrate to enzyme and signal substance to receptor, chelating structures to amino-acid residues on a surface, borates (react with sugars), aromates (bind to aromatic regions), antibodies (against antigenic epitope) and lectins (for reaction with a glycosylic epitope).

Sensor surface herein refers to a sensing or measurement surface or area of, or analogous to the type that may be present in a biosensor (according to the definition given above) based upon the detection of changes in the physico-chemical properties of a surface layer. Such surfaces will be discussed in more detail below.

The present invention thus relates to a method of charecterizing a macromolecule by studying its interactions with ligands, and is characterized in that it comprises determination of the mutual influence of ligand interactions by, after the macromolecule has interacted with at least one ligand, contacting the macromolecule with at least one additional ligand, either the macromolecule or the additional ligand(s) having been bound to a sensor surface, determining interaction by detecting a consequential change in the Physico-chemical properties of the sensor surface, and on the basis of the determined mutual dependence between the ligand interactions discriminating between epitopes of the macromolecule and mapping their relative positions.

By this method, due to the use of "biosensor" technique, an extraordinarily rapid and simple determination of surface-structural elements of the macromolecule is achieved. Further, the "biosensor"-based detection of the ligand interactions implies that the ligand or the macromolecule need not be labelled with detectable markers, since the molecule itself contributes to physico-chemical changes on the sensor surface. Although the inventive method does not provide the same structural information as, for example, X-ray diffraction methods, it may be performed with a substantially smaller amount of substance and in many cases without any preceding purification and constitutes an extraordinary complement to such methods in the work of accumulating structural information from unknown molecules. The method may also be used to identify changes of epitope structures, e.g., as a marker in the study of structural effects of chemical modifications.

The macromolecule or ligand is bound to the sensor surface through a biospecific ligand or chemically, whereby is intended all kinds of chemical bonding, such as covalent bonding, ion bonding, dipole bonding, hydrogen bonding and van der Waal forces. Thus, the macromolecule may, e.g., be bound covalently to the surface via any suitable coupling group depending on the macromolecule studied and the sensor surface used. When binding the macromolecule via a ligand the latter may be one of the ligands studied, as will be described in more detail below. By such biospecific binding of the macromolecule to the surface via a coupling group or a ligand the latter will function as a handle or spacer and place the macromolecule at a certain distance from the surface, so that also epitopes near the epitope utilized to immobilize the macromolecule to the surface will be exposed and accessible for interactions with an additional ligand or additional ligands. Hereby solution conditions for the macromolecule are simulated simultaneously as the advantages of a solid phase bound macromolecule may be utilized.

One embodiment of the above defined general method according to the invention comprises the steps of a) binding a ligand to a sensor surface, b) permitting the macromolecule to interact with the ligand bound to the sensor surface for binding the macromolecule to the sensor surface, c) sequentially contacting one or more additional ligands with the macromolecule bound to the sensor surface, and d) after the contact of each additional ligand with the sensor surface carrying the macromolecule, determining the interaction of the respective ligand With the macromolecule by detecting a consequential change in the physico-chemical properties of the sensor surface.

In order to obtain additional functional/structural information of macromolecules, steps c) and d) may be repeated one or more times with the various ligands added in an altered relative sequence, as will be described in more detail below. Also the binding ligand may be varied, if desired. It is also possible to repeat steps c) and d) above with altered ligand order, then change the binding ligand, again alter the sequence of steps c) and d), etc.

Another embodiment of the method according to the invention comprises the steps of a) binding the macromolecule to a sensor surface, b) sequentially contacting at least two ligands with the macromolecule bound to the sensor surface, and c) after the contact of each ligand with the sensor surface carrying the macromolecule, determining the interaction of the respective ligand with the macromolecule by detecting a consequential change in the physico-chemical properties of the sensor surface.

As in the preceding embodiment additional functional/ structural information of the macromolecule may, of course, be obtained if steps b) and c) are repeated one or more times with the various ligands added in an altered sequence. Still another embodiment of the method according to the invention comprises the steps of a) binding a ligand to a sensor surface, b) permitting the macromolecule to interact with at least one other ligand, c) contacting the macromolecule that has interacted with said at least one other ligand with the ligand-carrying sensor surface, and d) determining the interaction of the macromolecule with the ligand bound to the sensor surface by detecting a consequential change in the physico-chemical properties of the sensor surface.

As in the preceding embodiments additional functional/structural information of the macromolecule may be obtained if the ligand reactions are repeated one or more times with the various ligands in an altered relative sequence.

In a variation of the last-mentioned embodiment a sensor surface is used which has a plurality of sensing surfaces or areas, e.g. of the type described in our copending PCT-application entitled "Sensor unit and its use in biosensor systems" (based upon Swedish patent application No. 8804074-6) the disclosure of which is incorporated by reference herein, each of the various ligands studied being bound to a respective sensing surface. The macromolecule having at least one of the various ligands bound thereto is then successively contacted with the multifunctional sensing surface obtained, and the interaction of the macromolecule with all the sensing areas of the sensor surface is then determined for each macromolecule/ligand combination. The determination may in this case be performed with a multi-channel instrument adapted to the sensor surface, for example of the type described in our copending PCT-application entitled "Optical biosensor system" (based upon Swedish patent application No. 8804075-3), the disclosure of which is incorporated by reference herein.

When a greater number of ligands are studied, the ligand reaction steps in the above described embodiments may advantageously be successively performed with smaller groups of the ligands.

As is apparent from the description furnished above, the method of the present invention is based upon the study of functional domains (function not being limited to biofunction) of the macromolecule. On the basis of the specificity of the ligands qualitative as well as quantitative structural information about the macromolecule may be obtained. By the sequential execution of the ligand interactions with the macromolecule the method also implies studying how the interaction of one ligand with a functional domain will affect the interaction of another functional domain with another ligand. In the event of influence it may be an inhibiting and/or enhancing effect on the interaction. A greater resolution may be obtained by studying affinity changes in the interaction with biosensor technique. On the basis of these studies, functional information is obtained from which conclusions of structural elements of the macromolecule may be drawn. With the method of the invention it is thus possible to (i) identify one or more functional/structural elements of the macromolecule and (ii) locate the latter in relation to one or more other identified structural elements.

The ligands used simultaneously in the method may be of the same kind, e.g. monoclonal antibodies, but may also be of two or more different kinds, e.g., both antibodies, lectins and natural ligands. An example of the first-mentioned case is the mapping of antigenic epitopes on a protein by means of a set of, preferably monoclonal, antibodies, while the second case may be exemplified by the detection and location of different types of functional domains on a protein, e.g. antigenic epitopes, specific glycolysated structures and active sites. In order to obtain the relative positions of the functional/structural domains the natural ligand (biospecific partner) to the macromolecule may also be used as the ligand.

In the simplest case of carrying out the method of the invention, the macromolecule is studied with respect to only two ligands. In accordance with the different embodiments mentioned above, for the case that one ligand will bind to the sensing surface, the interaction determination at the sensing surface may be performed either upon the addition of the other ligand after the macromolecule has first bound to the sensing surface via said first ligand, or upon the addition of the macromolecule after the second ligand bound to the macromolecule. Of course, information of non-interaction is as valuable as detected interaction. If instead other binding of the macromolecule to the sensing surface is utilized than with one of the studied ligands, the interactions of the latter will be determined in sequence, i.e. as in the first-mentioned case the second ligand may interact with the macromolecule when the first ligand has been bound to the macromolecule. If it is already known that the two ligands may interact with the macromolecule, the sequential interactions with the macromolecule will provide information of how the ligand interactions influence each other. Herefrom, conclusions of the mutual relationship of the respective epitopes may be drawn. Optionally, the method steps in question may be repeated with the ligand interactions in an altered sequence. In case one ligand has first been used for binding the macromolecule to the sensing surface such reversed sequence, of course, means that the other ligand will then instead be used for binding the macromolecule to the sensing surface.

Although the above mentioned embodiment of studying the macromolecule in respect of only two ligands per se could be performed with, for example, blotting technique, ELISA or RIA (however, in a considerably more complicated and time-consuming manner), this will be practically impossible when using more ligands. It will be appreciated that in such cases the rapidity and simplicity of the method of the invention may be benefited from to a still greater extent.

As an example of the use of a plurality of ligands with the method of the invention may be mentioned the above indicated case of determining independent antigenic binding sites on a protein by means of a great number of monoclonals produced against the protein; this may be valuable, e.g., for the construction of a monoclonal-based test for the protein in question. In such a case one of the monoclonals may be used for binding the protein to the sensing surface, whereupon each one of the other monoclonals is first tested individually in respect of the protein immobilized by one of the monocionals. This step may be said to be a repeated performance of the above described case of determination in respect to only two ligands. Then the positively interacting monoclonals are analyzed further in various mutual combinations, e.g. in groups of five, which after one another may interact with the protein already immobilized via the original binding ligand.

By this procedure it will become evident whether a previously bound antibody blocks the binding site of a following one. Depending on the preceding interaction the antibodies will change their interactions with the epitopes in question, i.e. the antigenic binding sites on the protein surface. In the ideal case the method is, of course, to be carried out such that all the antibodies are cross-tested against each other. When the number of ligands is great the amount of determinations will, however, be relatively considerable, and adequate information would in practice be obtained by a suitable choice of tested ligand combinations. The monoclonals that have interacted negatively with the protein immobilized by one of the ligands are then analyzed sequentially in analogous manner but using other monoclonals for the binding to the sensing surface. Optionally, the binding monoclonals may also be changed one or more times in the analysis of the positively interacting monoclonals.

After a number of monoclonal combinations has been obtain in such a systematic manner, simple, logical and efficient presentation of the results will permit the antibody-binding surfaces of the protein to be identified and mutually related to each other. The method just described for the characterization of a protein with respect to antibody interactions is, of course, generally applicable to all types of ligands and macromolecules exhibiting a high specificity in their epitope interactions.

As is apparent from the information furnished above an essential feature of the method of the invention is the possibility of repeating the sequential analysis of the ligand interactions in loops, (i) with an altered sequence of the ligands supplied to the sensing surface, and (ii) with an altered binding site on the macromolecule, possibly in combination, to obtain improved functional/structural information about the macromolecule. While changing the relative order of the added ligands will permit better information to be obtained of the mutual relationship of the corresponding epitopes in functional and structural respects, one may, by varying the binding site on the macromolecule for immobilizing it to the sensing surface during the, more or less rotate the macromolecule on the sensing surface. In this way all parts of the macromolecule may be efficiently exposed to ligand interaction, thereby eliminating the possible influence that the proximity of an epitope to the sensing surface might have on the function of the epitope.

It will be appreciated that the method of the present invention may be used for obtaining qualitative functional/structural information about a macromolecule that is completely or partially unknown in this respect. The measurement principle of the method, however, also makes it possible to obtain quantitative information, e.g., where one or more epitopes of the macromolecule are previously known.

A contemplated important use of the method of the invention is for studying the influence of modifications of the primary structure of a macromolecule. Hereby, for example, point mutations or deletions of peptide sequences may be accomplished and epitope mapping in accordance with the invention may then be used to demonstrate which epitopes are influenced structurally such that their binding characteristics are changed. Such a modification of the macromolecule structure may be performed in order to change the properties of the molecule in one direction or another, so-called protein engineering, but also in order to obtain improved structural information about a partially known macromolecule.

Another use is for locating epitopes to known units by studying fragments of a macromolecule. A further conceivable use may be controlling of whether a macromolecule has been affected by a process such that an epitope has disappeared or a new epitope has been formed (neoepitope).

The structural analysis according to this invention can also be used for studies of macromolecules in patients serum/plasma/blood, urine, cerebrospinal liquid, saliva or in tissue. Thus, by characterization of a macromolecule from a patient with a subset of ligands according to the present method, different epitope patterns or epitope densities can be disclosed in relation to sickness or pathological condition. Such a difference in the structure of antigens in patients can be a result of post-translational modification such as glycosylation or proteolytic cleavage and reflect different cell origin for the antigen. An example of this is the tumour-associated antigen defined by the classical monoclonal antibodies such as CA 50, CA 19-9 or CA 242. The antigen is a glycoprotein with approximately 90% carbohydrate and a core protein of about 100 KDalton in molecular weight. By the method of the invention, better clinical correlation may be obtained if the tumour-associated antigen is characterized by a series of ligands and the binding of these different ligands is compared for epitope density and structural relations.

Epitope mapping is also of diagnostic interest when an immunological response to a given antigen is analyzed. By the described method and a subset of monoclonal antibodies or other ligands against defined epitopes on the antigen, the immunogenic response in a patient can be analyzed by characterization of the epitopes by the ligands after binding of the patient's polyclonal antisera to the antigen. The method with sequential injections of ligands to defined epitopes after quantification of the patient's immune response will easily characterize the epitope repertoire for the patient and this information can be correlated with pathological conditions and have a prognostic value. Other situations when epitope characterization with the method is of diagnostic or prognostic value are analyses of epitope immunogenic responses in patients in relation to vaccination. The epitope repertoire is of clinical interest for autoantigen as well as for foreign antigens.

As mentioned previously, the method of the invention may also, at least to some extent, be applied to impure macromolecule preparations. In the following will be described the use of the method according to the invention to obtain structural information about an impure antigen by means of monoclonal antibodies obtained when immunizing with the impure antigen.

If, for the sake simplicity, it is assumed that the impure antigen is a mixture of the proteins A, B and C, monoclonal antibodies directed against various epitopes thereof will be obtained in the immunization. In accordance with the present invention, one of the antibodies is bound to the sensing surface, and the protein mixture is subsequently added to biospecifically immobilize on the sensing surface of the protein, say A, that the antibody bound to the sensing surface is directed against. The sensing surface obtained is then used to investigate the other antibodies with regard to those binding to A. The antibodies that do not bind may be directed either against the same epitope on A as the antibody bound to the sensing surface or against protein B or C.

When an antibody binding to A has been found, the protein A is instead immobilized to the sensing surface via this other antibody, and all the previously obtained antibodies which are negative against the protein A are then screened against the antibody-immobilized protein A to find those antibodies binding to the same epitope on the protein A as said first antibody. The non-binding antibodies found must be directed against the protein B or C, and the above described procedure is repeated in analogous manner to identify these proteins. Once all the antibodies against the various proteins have been identified, each protein may be subjected to epitope mapping in accordance with the invention as described previously. Which component is responsible for the biological effect may easily be identified by way of inhibition with the antibodies.

The sensor surface used in the method of the invention may be any surface whose physical or chemical properties will be changed in a measurable manner by the ligand interactions in question. It may, for example, have a surface layer or a layer located near the surface where changes in optical properties, such as in the emitted amount of light or the wave length thereof, refractive index, etc., may be determined. Changes in the refractive index may, e.g., be measured by the previously mentioned SPR or ellipsometry techniques. The sensor surface may also be one for which the ligand interactions give rise to measurable changes in the photo-acoustic properties thereof. In other examples the biosensor surface is part of a piezoelectric crystal or field-effect transistor.

The total sensor system in which the sensor surface used in the method of the invention is included will, of course, depend on the kind of the sensor surface and the surface parameter studied. A suitable sensor system based upon SPR technique is described in our aforesaid copending PCT-application entitled "Optical biosensor system". The more detailed design thereof will appear from the following example.

Optionally the information obtained in the method of the invention may be computer processed to simplify the intepretation of the surface characteristics of the macromolecule in question, and the result may advantageously be presented in graphical form.

Figure 1B:
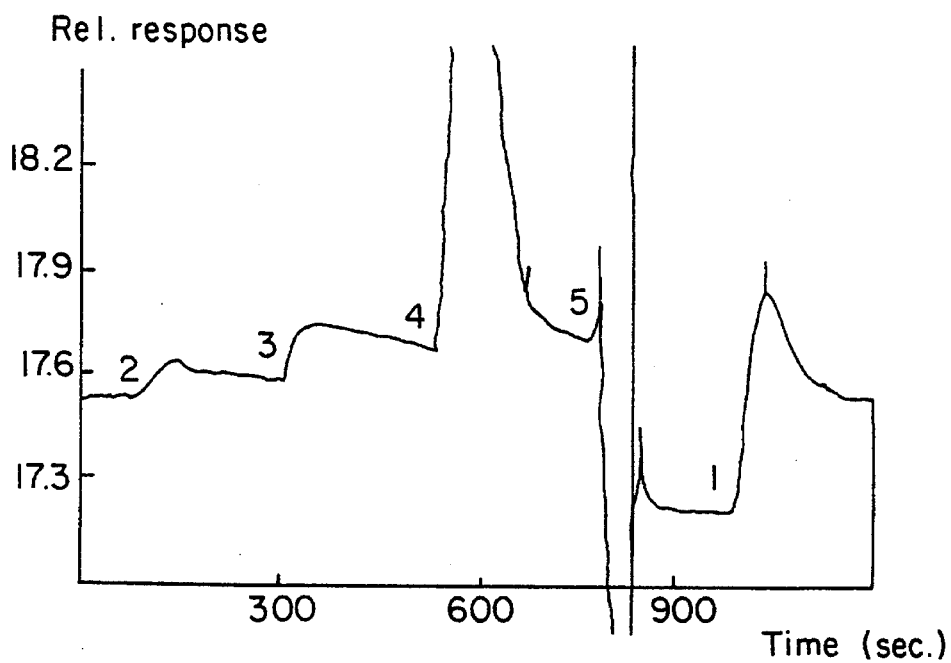
Figure 2A:
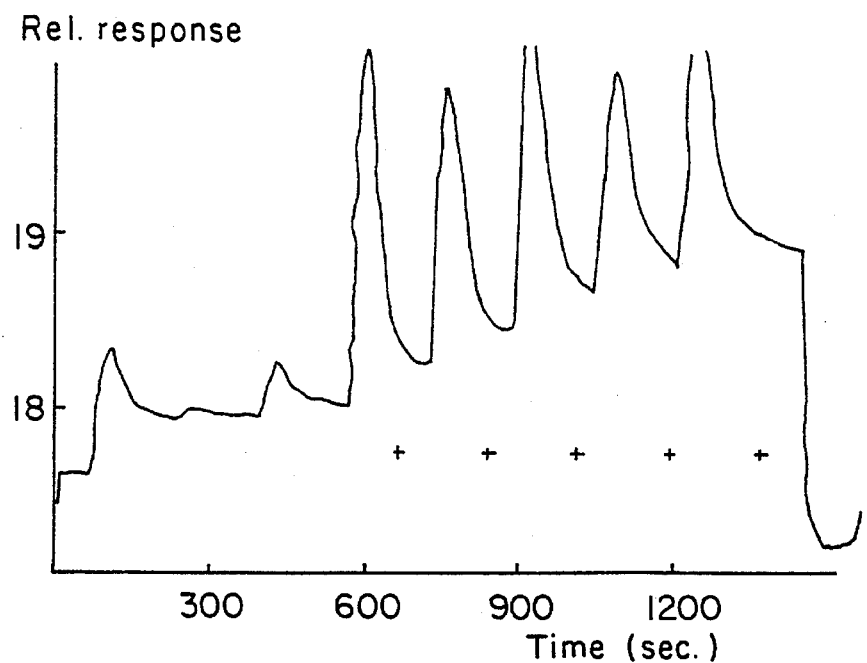
Figure 2B:
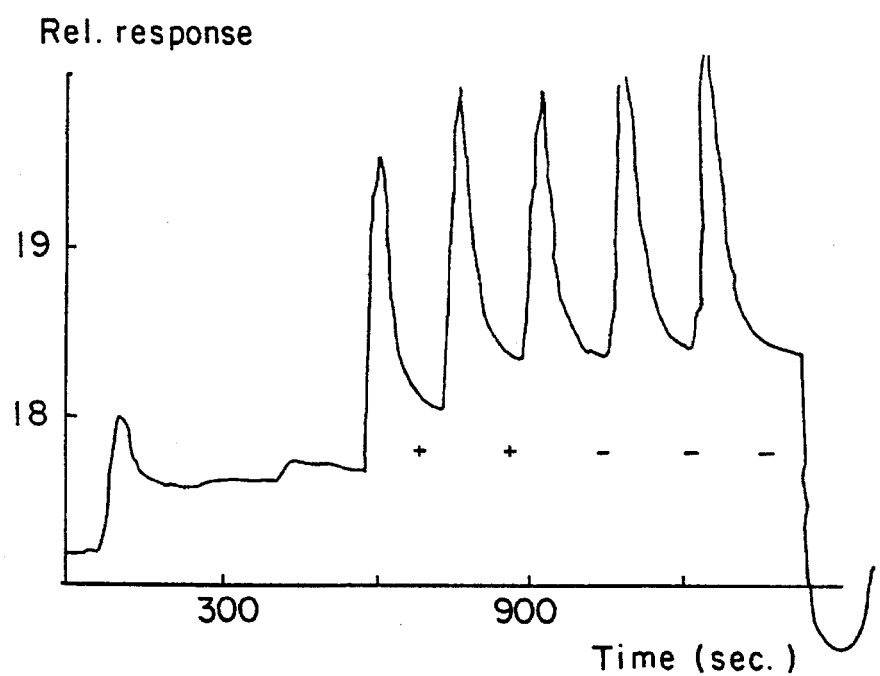
Figure 3:
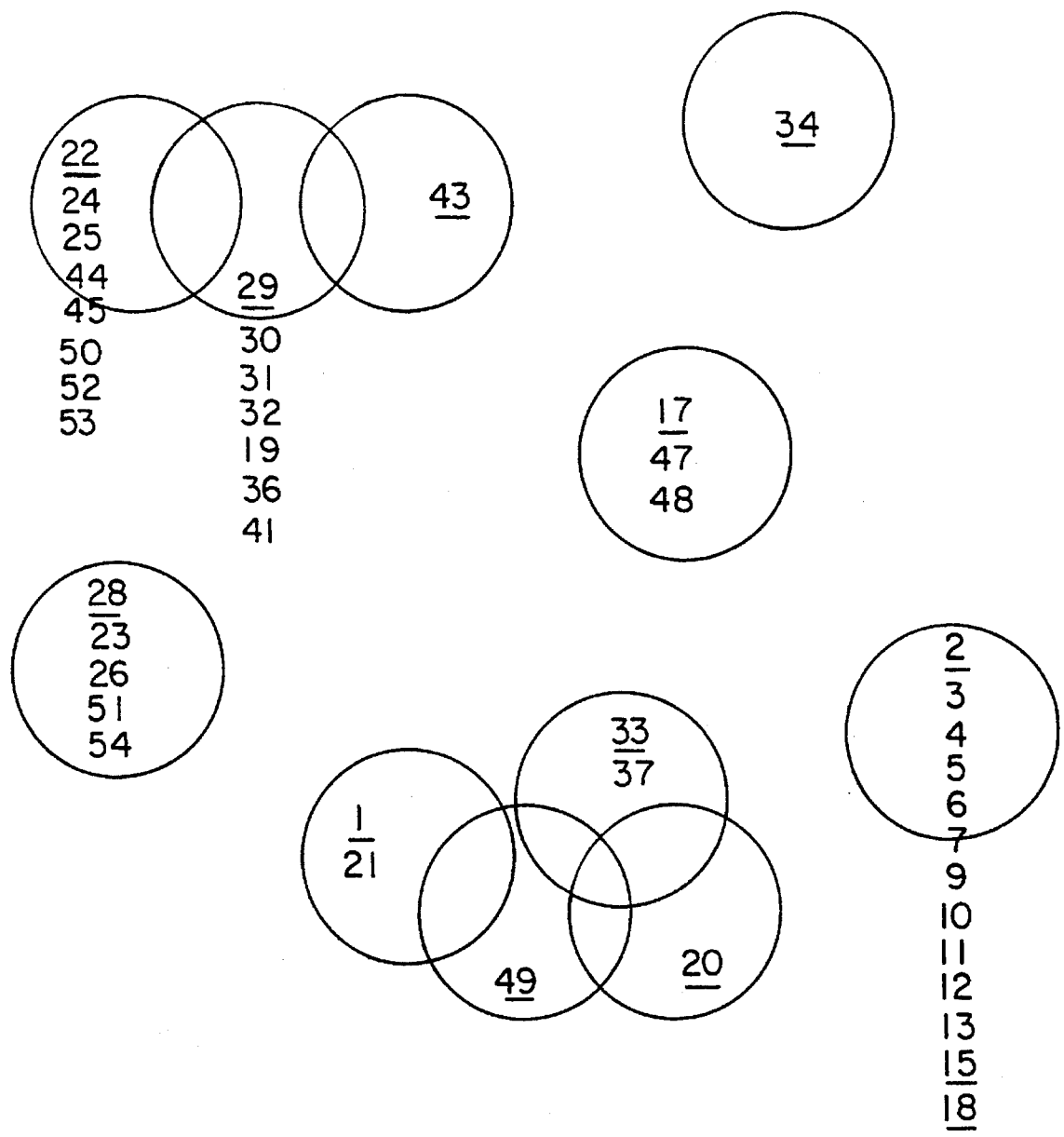

The invention will be further illustrated in the following example. In connection herewith reference is made to accompanying drawings, in which FIGS. 1a and 1b are graphs showing the surface change responses obtained when performing different steps of one embodiment of the method of the invention;

FIGS. 2a and 2b are similar graphs as FIGS. 1a and 1b showing the surface change responses obtained in another embodiment of the method of the invention; and FIG. 3 is an example of a schematic graphical illustration of the information obtained by the method of the invention.

EXAMPLE

In this example will be described epitope mapping of HIV-protein P24 by means of the method according to the invention. This protein is at present of very great interest, since the presence of the protein itself or antibodies directed against it is considered to be an early indication of HIV-infection. For the construction of a test system it is, of course, important to know several independent binding sites on the protein.

For the epitope mapping an optical biosensor system described in our aforesaid PCT-application entitled "Optical biosensor system" was used. This biosensor system, which in one embodiment is based upon SPR technology known per se, has a replaceable sensor unit; a block unit for liquid handling having a conduit or channel system which transports the reagent and sample solutions over the sensing surface of the sensor unit; an optical unit which couples incident light rays to the sensitized surface and detects the reflected radiation; and an evaluation unit which after calibration transforms the detector signal into a parameter proportional to the amount of substance at the sensing surface. When performing a measurement, a defined sample liquid volume is introduced by injection into a defined channel section, which liquid volume is then by means of eluent liquid forced to pass the sensing surface for optical analysis. The instrument used here had a measuring channel of 0.5×0.05×4 mm. As pump was used a modified variation of the pump marketed by Pharmacia AB, Sweden, under the designation P500. An auto-injector Gilson Model 231 with a 50 µl extern loop was coupled to the instrument.

The sensor unit consisted of a glass plate coated with a thin gold film to which had been bound a layer of dextran hydrogel as described in our copending PCT-application entitled "Sensing surfaces capable of selective biomolecular interactions to be used in biosensor systems" (based upon Swedish patent application No. 8804073-8), the disclosure of which is incorporated by reference herein, and which then had been modified as described in our aforesaid copending PCT-application entitled "Sensor unit and its use in biosensor systems" and is specified below.

The detector device comprised a set of detector elements in the form of photo-diodes having a width of 80µ and spaced at 20µ intervals. The unit "diode(s)" used hereinafter for the mass adsorption at the measuring surface (the response) is associated to this particular photo-diode arrangement and indicates the number of successive photo-diodes embraced by the resonance change in angle caused by the refractive index change of the sensing surface.

For the determination, protein P24 obtained by recombinant DNA technique as well as 54 culture media containing anti-P24 monoclonals with reactivity against this protein were used.

Prior to the actual epitope determination subclass and concentration determination on these 54 culture media were performed as will be described below.

As the eluent was used 10 mM Hepes, 0.15 NaCl, 3.4 mM EDTA, 0.1% FT 229, pH=7.4. Reagent and sample were injected in volumes of 20 µl, and regeneration was performed with 0.1M glycine-HCl, pH=2.5, 0.1% FT 229 (20 µl).

A. Subclass determination

For this determination the dextran treated sensing surface was modified by carboxymethylation, and reactive ester groups were subsequently introduced by incubation with N-hydroxysuccinimide and N-(3-dimethylaminopropyl)-N'-ethyl-carbodiimide hydrochloride (EDC). To the sensing surface derivatized in this way, rabbit anti-mouse light chains from an immunosorbent-purified preparation were coupled.

The following anti-mouse IgG-subclass reagents were used:

Rat monoclonal anti-G1, rat monoclonal anti-G2a, rat monoclonal anti-G2b and rat monoclonal anti-G3 obtained from MIAB, Uppsala, Sweden. The reagents were diluted to 100 µg/ml in 10 mM Hepes, pH=7.4.

The 54 culture media were successively analyzed, the anti-subclass reagents being run sequentially in the order anti-G3, anti-G2a, anti-G2b and anti-G1. The flow was 20 µl/min, and the time between the injections was 2 minutes.

A culture medium was defined as G1 when the response for anti-G1 amounted to at least 0.1 diode. All culture media except No. 8, 51, 27, 35, 38, 39, 40, 41, 43 and 46 exhibited response values exceeding 0.1. The response for anti-G3, anti-G2a and anti-G2b did not exceed 0.02 diode for any culture medium. The injection of purified IgM (100 µg/ml) resulted in responses less than 0.03 for all anti-subclass reagents.

B. Concentration determination

All culture media were correlated to a G1-based standard curve established on the basis of response values obtained with a mix of G1-monoclonals (anti-beta-2-macroglobulin) diluted in culture medium (5% FCS) to the concentrations 2, 5, 10, 20, 30, 40, 50, 60, 80 and 100 µg/ml, respectively.

The standard points were run in duplicate, and a standard curve based upon the mean value of each point was established in the interval 2–30 µg/ml. The same sensing surface as in the subclass determination above was used; the flow was 20 μl/min. and the time between the injections was 3 minutes. The measurements on the culture media were performed with single samples. The culture media 8, 27, 35, 38, 40 and 41 showed very low concentrations.

C. Epitope studies

On the basis of the above performed subclass and concentration determinations the following culture media were excluded from the epitope studies: 8, 16, 27, 35, 38, 39 and 40. The other culture media were characterized in respect of mutual epitope reactivity as will be described below. For these determinations the dextran treated sensing surface was modified as follows:

C1. Introduction of hydrazide functions 3.5 g bromoacetic acid were dissolved in 27 g of 2M sodium hydroxide solution. The mixture was poured over a dextran-treated and carboxymethylated sensor surface and incubated for 16 hours at 25° C. in a shaker incubator. The surface was washed with water, whereupon the aforesaid procedure was repeated once. After washing, the surface was treated for 5 minutes with 0.8 g of N-(3-dimethylaminopropyl)-N'-ethyl-carbodiimide hydrochloride (EDC) in 20 ml of water, this being then followed by an addition of 4.0 ml of hydrazine hydrochloride in 20 ml of water. The surface was incubated for 16 hours in a shaker incubator at 25° C. and then washed with water.

C2. Coupling of rabbit-anti-mouse-$F_{c\gamma}$ to the derivatized measuring surface Immunosorbent-purified rabbit anti-mouse-$F_{c\gamma}$ in 10 mM acetate buffer, pH 5.5, was coupled during 20 minutes to the hydrazide surface obtained above, whereupon unbound antibody was removed by rinsing the surface in PBS buffer, pH 7.4, and in 0.1M glycine, pH 2.5. The coupling obtained corresponded to a response in the measuring equipment of about 2.5 diodes.

A flow of 20 μl/min. and 3 min. between the injections were used for the experiment.

C3. Epitope mapping

As a first step culture medium No. 12 (diluted 1:4) was injected to immobilize the corresponding monoclonal on the sensing surface. To block any remaining binding sites on the sensing surface a G1-monoclonal irrelevant in the context, viz. anti-beta-2-microglobulin (40 μg/ml), was then injected, whereupon the HIV-protein P24 (10 μg/ml) was injected. This protein bound biospecifically to the surface via the monoclonal 12, and the system was then ready for analysis of interaction with the other monoclonals. In a first analysis series the binding of each monoclonal individually was studied with regeneration of the system between each measurement.

As a result, the culture media were distributed among two groups:

a) those reacting with P24 indepedently of medium No. 12: 1, 17, 19, 20, 21, 22, 23, 24, 25, 26, 28, 29, 30, 31, 32, 33, 34, 36, 37, 41, 43, 44, 45, 47, 48, 49, 50, 51, 52, 53 and 54; and b) those not reacting with P24 when medium No. 12 has bound: 2, 3, 4, 5, 6, 7, 9, 10, 11, 12, 13, 14, 15, 18 and 42.

Case a) above is illustrated in the accompanying FIG. 1a and case b) in FIG. 1b where the y-axis shows relative response and the x-axis the time in seconds. In both figures the numeral 1 indicates the injection of culture medium No. (for technical reasons the injection was made last in each cycle; no regeneration was then made, and the monoclonal was therefore already bound to the surface when injection No. 2 was performed); 2 indicates the injection of anti-beta-2-microglobulin, 3 indicates the injection of P24, 4 indicates the injection of P24-reactive culture medium that binds to P24 independently of medium No. 12 (FIG. 1a) or that competes with medium No. 12 (FIG. 1b), and 5 indicates regeneration. In the measurements a positive response is defined as a diode reading greater than 0.13 diode, but a negative signal must not exceed 0.02 diode.

The positive media were then analyzed further in various mutual combinations, several media being injected sequentially. The various combinations and the results obtained are shown in Table 1 below. In the table the responses exceeding 0.13 diode are indicated by "+". A response below 0.02 diode is designated by "−". In certain cases the response is between the two existing limits (half +).

TABLE 1

"12+"-clones tested against clone 12

| | Medium No. | Response | | Medium No. | Response | | Medium No. | Response |
|---|---|---|---|---|---|---|---|---|
| 1) | 1 | + | 2) | 1 | + | 3) | 22 | + |
| | 17 | + | | 1 | − | | 23 | + |
| | 19 | + | | 21 | − | | 24 | − |
| | 20 | + | | | | | 25 | − |
| | 21 | − | | | | | 26 | − |
| 4) | 23 | + | 5) | 25 | + | 6) | 23 | + |
| | 24 | + | | 26 | + | | 26 | − |
| | 25 | − | | 23 | − | | 25 | + |
| | 26 | − | | | | | | |
| | 22 | − | | | | | | |
| 7) | 28 | + | 8) | 29 | + | 9) | 33 | + |
| | 29 | + | | 30 | − | | 34 | + |
| | 30 | − | | 31 | − | | 36 | ?* |
| | 31 | − | | 32 | − | | 37 | − |
| | 32 | − | | 28 | + | | 41 | − |
| 10) | 36 | + | 11) | 37 | + | 12) | 41 | + |
| | 33 | + | | 41 | + | | 36 | − |
| | 34 | + | | 36 | − | | 33 | + |
| | | | | 33 | − | | 37 | − |
| | | | | 34 | + | | | |
| 13) | 43 | + | 14) | 44 | + | 15) | 49 | + |
| | 44 | + | | 45 | − | | 50 | + |
| | 45 | − | | 48 | + | | 51 | + |

TABLE 1-continued

"12+"-clones tested against clone 12

| Medium No. | Response | Medium No. | Response | Medium No. | Response |
|---|---|---|---|---|---|
| 47 | + | 47 | − | 52 | − |
| 48 | − |  |  | 53 | − |
| 16) 51 | + | 17) 53 | + | 18) 54 | + |
| 52 | + | 51 | + | 53 | + |
| 53 | − | 52 | − | 51 | − |
| 50 | − | 54 | − |  |  |
| 49 | + |  |  |  |  |
| 19) 1 | + | 20) 22 | + | 21) 29 | + |
| 22 | + | 43 | + | 22 | − |
| 28 | + | 17 | + | 43 | − |
| 33 | + | 29 | − |  |  |
| 43 | + | 34 | + |  |  |
| 22) 17 | + | 23) 22 | + | 24) 19 | + |
| 29 | + | 43 | + | 36 | − |
| 43 | − | 19 | − | 22 | − |
| 22 | − | 36 | − | 43 | − |
|  |  | 49 | + | 49 | + |
| 25) 22 | + | 26) 43 | + | 27) 29 | + |
| 19 | half+ | 19 | half+ | 19 | − |
| 43 | − | 22 | − |  |  |
| 28) 49 | + | 29) 20 | + | 30) 23 | + |
| 43 | + | 43 | + | 43 | + |
| 34 | + | 34 | + | 34 | + |
| 17 | + | 17 | + | 17 | + |
| 22 | + | 22 | + | 22 | + |
| 31) 44 | + | 32) 47 | + | 33) 20 | + |
| 43 | + | 43 | + | 23 | + |
| 34 | + | 34 | + | 44 | + |
| 17 | + | 17 | − | 50 | − |
| 22 | − | 22 | + |  |  |
| 34) 50 | + | 35) 1 | + | 36) 28 | + |
| 23 | + | 43 | + | 43 | + |
| 44 | − | 34 | + | 34 | + |
| 20 | + | 17 | + | 17 | + |
|  |  | 22 | + | 22 | + |
| 37) 33 | + | 38) 51 | + | 39) 49 | + |
| 43 | + | 43 | + | 1 | − |
| 34 | + | 34 | + | 28 | + |
| 17 | + | 17 | + | 33 | − |
| 22 | + | 22 | + | 20 | − |
| 40) 1 | + | 41) 20 | + | 42) 23 | + |
| 49 | − | 49 | − | 1 | + |
| 33 | + | 28 | + | 33 | + |
|  |  |  |  | 28 | − |
| 43) 20 | + | 44) 51 | + |  |  |
| 33 | − | 1 | + |  |  |
|  |  | 33 | + |  |  |
|  |  | 28 | − |  |  |

*sweep error

FIGS. 2a and 2b, respectively, show the detector response in such an experiment where 5 monoclonals were sequentially injected and all of them bind independently of the fact that the preceding monoclonal has bound. In FIG. 2b the first and the second monoclonals are bound (+), while the other binding sites for the other three monoclonals are blocked (−).

The negative media were analyzed in analogous manner as the positive media but with medium No. 30 immobilized in the first step instead of medium No. 12. In an initial experiment it was verified that the individual media reacted with a positive response, medium No. 12 and medium No. 42 reacting with a response outside the limits set. These two media were analyzed with the same result in a sequence with medium No. 34 immobilized in the first step. The media were then analyzed in the combinations and with the results indicated in Table 2 below. The same judgement criteria apply as for Table 1 above.

TABLE 2

"12+"-clones tested against clone 12

| | Medium No. | Response | | Medium No. | Response | | Medium No. | Response |
|---|---|---|---|---|---|---|---|---|
| 1) | 14 | + | 2) | 2 | + | 3) | 15 | + |
| | 2 | half+ | | 3 | – | | 6 | – |
| | 3 | – | | 4 | – | | 7 | – |
| | 4 | – | | 5 | – | | 9 | – |
| | 5 | – | | 14 | – | | 10 | – |
| 4) | 18 | + | 5) | 42 | half+ | 6) | 18 | + |
| | 11 | – | | 14 | half+ | | 15 | – |
| | 12 | – | | 15 | half+ | | 2 | – |
| | 13 | – | | 128 | – | | | |
| | 42 | – | | | | | | |
| 7) | 42 | half+ | 8) | 3 | + | | | |
| | 14 | half+ | | 18 | – | | | |
| | 15 | half+ | | 10 | – | | | |
| | | | | 6 | – | | | |
| | | | | 2 | – | | | |

When all the results had been compiled the characterization performed could diagramatically be illustrated as is shown in FIG. 3. When the culture medium number in the figure is underlined it indicates that the medium was tested against all other underlined media. As appears from FIG. 3 six major domains containing independent binding sites could thus be identified. It is to be noted that the characterization is incomplete since all individual media were not tested against all the others. This may result in certain media having their reactivity directed against a very close but not identical epitope.

The above described epitope studies revealed a surprisingly great number of epitopes on the P24 molecule and that there is simultaneously room for at least 6 antibodies thereon. The result of the studies may, for example, be used for the development of suitable monoclonal combinations for diagnostic tests.

The invention is, of course, not restricted to the embodiments particularly described above, but many modifications and changes are within the scope of the general inventive concept as it is defined in the subsequent claims.

We claim:

1. A method of discriminating between and mapping epitopes of a macromolecule by studying its interactions with ligands, comprising the steps of:

determining blocking or non-blocking of the epitopes by the ligands by, after the macromolecule has interacted with at least one ligand, sequentially contacting the macromolecule with at least two additional ligands, either the macromolecule or one of the at least two additional ligands having been bound to a sensor surface;

determining ligand binding interaction by detecting a change in the physico-chemical properties of the sensor surface; and discriminating between epitopes of the macromolecule and mapping their relative positions on the basis of the determined blocking or non-blocking of the epitopes by the ligands.

2. The method according to claim 1, further comprising the steps of:

a) binding the macromolecule to a sensor surface;

b) sequentially contacting at least three ligands with the macromolecule bound to the sensor surface; and c) determining the ligand binding interaction after each one of the at least three ligands is contacted with the macromolecule by detecting the change in the physico-chemical properties of the sensor surface after each one of the at least three ligands is contacted with the macromolecule bound to the sensor surface.

3. The method according to claim 2, wherein steps b) and c) are repeated one or more times with the ligands in an altered sequence.

4. The method according to claim 1, further comprising the steps of:

a) binding the at least one ligand, specific to the macromolecule to the sensor surface;

b) permitting the macromolecule to interact with the at least one ligand bound to the sensor surface for binding the macromolecule to the sensor surface;

c) sequentially contacting the at least two additional ligands with the macromolecule bound to the sensor surface; and d) determining the ligand binding interaction after each one of the at least two additional ligands is contacted with the macromolecule by detecting the change in the physico-chemical properties of the sensor surface after each one of the at least two ligands is contacted with the macromolecule bound to the sensor surface.

5. The method according to claim 4, wherein steps c) and d), and optionally also a), are repeated one or more times with the ligands in an altered sequence.

6. The method according to claim 1, further comprising contacting the macromolecule with the at least one ligand and the at least two additional ligands at least one more time in an altered sequence.

7. The method according to claim 1, wherein a plurality of ligands is used, and the method is performed repeatedly with a subset of the ligands.

8. The method according to claim 1, wherein said change in the physico-chemical properties of the sensor surface is a change in the refractive index of the sensor surface.

9. The method according to claim 1, wherein the macromolecule is a protein.

10. The method according to claim 1, wherein the ligands comprise antibodies.

11. The method of claim 1, further comprising structurally modifying the macromolecule and studying influences of the structural modification on ligand binding properties of the macromolecule.

12. The method of claim 1, wherein the macromolecule is from a patient and said discriminating between and mapping epitopes of the macromolecule is used for diagnostic or prognostic clinical purposes.

13. The method of claim 12, which comprises characterizing the macromolecule with a subset of ligands defining different possible epitopes on the macromolecule, the presence or absence, respectively, of one or more of said epitopes on the macromolecule being indicative of a pathological condition.

14. The method according to claim 12, which comprises analyzing immune response by first contacting a macromolecule having defined epitopes with a patient sample, and then determining the possible blocking of one or more of the epitopes by macromolecules present in the sample by contacting the macromolecule having defined epitopes with a subset of ligands binding to said epitopes.

\* \* \* \* \*

UNITED STATES PATENT AND TRADEMARK OFFICE
CERTIFICATE OF CORRECTION

PATENT NO. : 5,554,541 Page 1 of 1
APPLICATION NO. : 08/366443
DATED : September 10, 1996
INVENTOR(S) : Magnus Malmqvist et al.

It is certified that error appears in the above-identified patent and that said Letters Patent is hereby corrected as shown below:

Item (30)
Foreign Application Priority Data, should include --PCT/SE1989/00644  11/09/89--

Signed and Sealed this

Fifth Day of June, 2007

JON W. DUDAS
*Director of the United States Patent and Trademark Office*